US012110972B2

(12) United States Patent  (10) Patent No.: US 12,110,972 B2
Nakagami et al.  (45) Date of Patent: Oct. 8, 2024

(54) FLOW PATH SWITCHING DEVICE

(71) Applicant: NIPRO CORPORATION, Osaka (JP)

(72) Inventors: Hiroyuki Nakagami, Osaka (JP); Minami Kawabe, Osaka (JP); Tomoe Morita, Osaka (JP); Issei Kamei, Osaka (JP)

(73) Assignee: NIPRO CORPORATION, Osaka (JP)

(*) Notice: Subject to any disclaimer, the term of this patent is extended or adjusted under 35 U.S.C. 154(b) by 197 days.

(21) Appl. No.: 16/753,705

(22) PCT Filed: Oct. 4, 2018

(86) PCT No.: PCT/JP2018/037219
§ 371 (c)(1),
(2) Date: Apr. 3, 2020

(87) PCT Pub. No.: WO2019/070028
PCT Pub. Date: Apr. 11, 2019

(65) Prior Publication Data
US 2020/0271232 A1  Aug. 27, 2020

(30) Foreign Application Priority Data

Oct. 6, 2017  (JP) .................................. 2017-196110
Oct. 6, 2017  (JP) .................................. 2017-196111

(51) Int. Cl.
*F16K 11/085*  (2006.01)
*A61M 1/36*  (2006.01)
*A61M 39/22*  (2006.01)

(52) U.S. Cl.
CPC ........... *F16K 11/0853* (2013.01); *A61M 1/36* (2013.01); *A61M 39/223* (2013.01); *Y10T 137/86654* (2015.04); *Y10T 137/86839* (2015.04)

(58) Field of Classification Search
CPC .............. F16K 11/0853; A61M 39/223; Y10T 137/86654; Y10T 137/86839
(Continued)

(56) References Cited

U.S. PATENT DOCUMENTS 2,229,931 A * 1/1941 Parker ..................... F16K 39/06
137/625.22
2,229,932 A * 1/1941 Parker ..................... F16K 39/06
137/625.43
(Continued)

FOREIGN PATENT DOCUMENTS

JP  S61-282676 A  12/1986
JP  H03-061774 A  3/1991
(Continued)

OTHER PUBLICATIONS

International Search Report for corresponding Application No. PCT/JP2018/037219, mailed Dec. 11, 2018.
(Continued)

*Primary Examiner* — Craig M Schneider
*Assistant Examiner* — Christopher D Ballman
(74) *Attorney, Agent, or Firm* — Renner, Otto, Boisselle & Sklar, LLP

(57) ABSTRACT

The flow path switching device includes: a body 100 including an outer cylinder 101 having four ports 111 and a plug 102 having two arc-shaped tunnel-like flow paths 121 each connecting adjacent two of four openings 102a formed in a side surface of the plug 102. The plug 102 is rotatable between a first position and a second position, the first position being a position in which one of the flow paths 121 connects adjacent two of the four ports 111 and the other flow path 121 connects the remaining two ports, and the second position being a position in which each of the flow
(Continued)

paths connects adjacent two of the ports 111 which are not connected when the plug 102 is located at the first position.

7 Claims, 11 Drawing Sheets

(58) Field of Classification Search
USPC .................................................. 137/625.47
See application file for complete search history.

(56) References Cited

U.S. PATENT DOCUMENTS

| | | | | |
|---|---|---|---|---|
| 2,362,389 | A * | 11/1944 | Martin | F16H 39/02 60/413 |
| 2,623,234 | A * | 12/1952 | Brown | E04D 13/0765 15/352 |
| 3,295,554 | A * | 1/1967 | Huppert | F16K 27/065 251/317 |
| 3,419,827 | A * | 12/1968 | Webb | H01P 1/122 74/96 |
| 3,535,874 | A * | 10/1970 | Smith | F02N 7/10 60/786 |
| 3,750,704 | A * | 8/1973 | Burke | F16K 11/0853 137/625.47 |
| 4,147,184 | A * | 4/1979 | Jess | F16K 5/0292 251/312 |
| 4,219,021 | A * | 8/1980 | Fink | A61M 39/223 137/556.6 |
| 5,046,528 | A * | 9/1991 | Manska | F16K 31/602 251/304 |
| 5,058,416 | A | 10/1991 | Engelhardt et al. | |
| 5,074,334 | A | 12/1991 | Onodera | |
| 5,423,751 | A * | 6/1995 | Harrison | A61M 5/16827 604/83 |
| 5,529,758 | A * | 6/1996 | Houston | F16K 11/0853 422/171 |
| 5,832,959 | A * | 11/1998 | Szymczakowski | A61M 39/223 251/297 |
| 6,202,696 | B1 * | 3/2001 | McPherson, Jr. | B05B 5/1616 251/368 |
| 6,536,742 | B2 * | 3/2003 | Lotz | A61M 39/223 251/312 |
| 6,698,452 | B2 * | 3/2004 | Sisk | F25B 41/26 251/174 |
| 7,232,428 | B1 * | 6/2007 | Inukai | A61M 39/02 604/248 |
| 7,695,445 | B2 * | 4/2010 | Yuki | A61M 39/223 604/4.01 |
| 7,713,246 | B2 * | 5/2010 | Shia | A61J 15/0092 604/249 |
| 7,815,588 | B2 * | 10/2010 | Sakiewicz | A61M 1/3656 251/231 |
| 7,963,951 | B2 * | 6/2011 | Kitani | A61M 39/223 137/625 |
| 8,534,321 | B2 * | 9/2013 | Ziv | F16K 11/0833 137/239 |
| 8,584,701 | B2 * | 11/2013 | Duncan | A61M 39/223 116/277 |
| 9,050,401 | B2 * | 6/2015 | Levy | A61M 5/19 |
| 9,212,751 | B2 * | 12/2015 | McLane | F01P 7/165 |
| 9,212,762 | B2 * | 12/2015 | Duncan | A61M 39/223 |
| 9,375,561 | B2 * | 6/2016 | Mansour | A61M 39/26 |
| 9,803,760 | B2 * | 10/2017 | Morein | F16K 11/0853 |
| 10,004,890 | B2 * | 6/2018 | Liu | A61M 39/223 |
| 10,344,877 | B2 * | 7/2019 | Roche | B60L 58/26 |
| 10,427,538 | B2 * | 10/2019 | Myers | F25B 9/04 |
| D886,953 | S * | 6/2020 | Gabriel | D23/245 |
| 10,960,135 | B2 * | 3/2021 | Tornblom | A61M 5/16881 |
| 2001/0047834 | A1 | 12/2001 | Menin et al. | |
| 2004/0168969 | A1 | 9/2004 | Sternby et al. | |
| 2009/0171261 | A1 | 7/2009 | Sternby et al. | |
| 2009/0314063 | A1 | 12/2009 | Sternby | |

FOREIGN PATENT DOCUMENTS

| | | |
|---|---|---|
| JP | H04-138136 A | 5/1992 |
| JP | H08-141072 A | 6/1996 |
| JP | 2000-274537 A | 10/2000 |
| JP | 2009-268922 A | 11/2009 |
| JP | 2017-046991 A | 3/2017 |

OTHER PUBLICATIONS

P. G. Sakiewicz et al, "Introduction of a Switch that Can Reverse Blood Flow Direction On-Line during Hemodialysis", ASAIO Journal, vol. 46, p. 464-p. 468 (2000) (cited in Specification).

* cited by examiner

FLOW PATH SWITCHING DEVICE

TECHNICAL FIELD

The present disclosure relates to flow path switching devices, and more particularly to a flow path switching device that switches the direction of flow paths in an extracorporeal circuit.

BACKGROUND ART

There are various medical procedures in which fluid such as blood is drawn or administered to or from a patient using various tube sets. One example of such a procedure is hemodialysis. In hemodialysis, blood is drawn from the patient's body through a vascular access, purified by a dialyzer, and returned to the patient's body. During hemodialysis, blood is typically drawn from a site upstream of the vascular access and the purified blood is returned to a site downstream of the vascular access. However, there are cases where blood is drawn from a site downstream of the vascular access and the purified blood is returned to a site upstream of the vascular access. Various kinds of information such as a vascular access flow rate can be obtained by reversing the direction of blood flow. For example, by using the information thus obtained, the state of the vascular access can be evaluated and prior warning about other health problems such as trouble with the vascular access can be obtained. Accordingly, a procedure such as repairing or replacing the vascular access can be performed on a patient who has been on dialysis for several years.

The direction of blood flow can be reversed by changing connection between tubes and the vascular access. However, changing connection between the tubes and the vascular access is complicated and tends to cause a medical accident. One proposed way to switch the direction of blood flow without changing connection between the tubes and the vascular access is to mount a switching device having four tubes and four clamps (see, e.g., Non-Patent Document 1). With such a switching device, the direction of blood flow in extracorporeal circulation can be switched between the normal direction and the reverse direction without changing connection between the tubes and the vascular access.

CITATION LIST

Patent Document

NON-PATENT DOCUMENT 1: P. G. Sakiewicz et al., "Introduction of a Switch that Can Reverse Blood Flow Direction On-Line during Hemodialysis," ASAIO Journal, Vol. 46, pp. 464-468, 2000

SUMMARY OF THE INVENTION

Technical Problem

In the conventional switch device, however, the four clamps must be correctly operated. Accordingly, this switch device is complicated to operate, and the operator tends to operate this switch device erroneously. It also takes time to switch the direction of blood flow.

It is an object of the present disclosure to implement a flow path switching device that is easy to operate.

Solution to the Problem

A first aspect of a flow path switching device according to the present disclosure includes: a body including an outer cylinder and a plug, the outer cylinder having a first port, a second port, a third port, and a fourth port which are provided at regular intervals along its outer circumference, the plug being accommodated in the outer cylinder such that the plug can slide and rotate therein, and the plug having two arc-shaped tunnel-like flow paths independent of each other and each connecting adjacent two of four openings formed at regular intervals in a side surface of the plug. The plug is rotatable between a first position and a second position, the first position being a position in which one of the flow paths connects the first port and the second port and the other flow path connects the third port and the fourth port, and the second position being a position in which one of the flow paths connects the first port and the fourth port and the other flow path connects the second port and the third port.

With this configuration, the direction of the flow paths in an extracorporeal circuit etc. can be switched by a single operation. This reduces medical accidents resulting from erroneous operation of the flow path switching device. The tunnel-like flow paths connect the openings formed in the side surface of the plug. This configuration allows a smoother blood flow as compared to the case where grooves or cutouts are formed in the side surface of the plug as flow paths. This configuration also reduces the contact region between the side surface of the plug and blood.

In the first aspect of the flow path switching device, the flow path may have a radius of curvature of 3.5 mm or more and 20 mm or less. With this configuration, blood smoothly flows through the flow paths.

In the first aspect of the flow path switching device, the outer cylinder may compress the plug. This configuration reduces the possibility of liquid leakage.

The first aspect of the flow path switching device may further include a click mechanism that gives an operator a feel of a click when the plug reaches the second position while the operator is rotating the plug from the first position toward the second position and when the plug reaches the first position while the operator is rotating the plug from the second position toward the first position. This configuration makes the operator clearly aware through the feel he or she gets while operating the plug that the direction of the flow paths has been switched. This configuration thus reduces the possibility of erroneous operation.

The first aspect of the flow path switching device may further include a rotation restriction mechanism that restricts a rotation range of the plug to up to 90° between the first position and the second position. With this configuration, the operator can switch the direction of the flow paths by operating the plug to the position where the plug stops. This configuration thus further reduces the possibility of erroneous operation.

The first aspect of the flow path switching device may further include a visual indication mechanism that makes the operator visually aware that the plug is located at the first position or the second position. With this configuration, the operator can easily visually verify completion of the switching operation. Moreover, the operator can easily check the current directions of the flow paths.

In the first aspect of the flow path switching device, the plug may have a recess for visual recognition in its upper surface, and a shape of the flow paths may be visually recognizable through the recess for visual recognition. With this configuration, the operator can easily tell whether the plug is located at the first position, the second position, or an intermediate position therebetween.

In the first aspect of the flow path switching device, the plug may have a grip portion with a cross shape in plan which has four protruding portions, and the four protruding portions of the grip portion and the four ports may extend in a same direction when the plug is located at the first position and the second position. With this configuration, the operator can intuitively recognize the first position, the second position, and the intermediate position therebetween from the positions of the protruding portions of the grip portion and the positions of the ports.

The first aspect of the flow path switching device may further include: a first tube connected to the first port, a second tube connected to the second port, a third tube connected to the third port, and a fourth tube connected to the fourth port; and a tube fixing portion that fixes the tubes such that the first tube connected to the first port and the third tube connected to the third port are extended to a same side as viewed in plan and the second tube connected to the second port and the fourth tube connected to the fourth port are extended to a same side, which is an opposite side from the side to which the first tube and the third tube are extended, as viewed in plan. With this configuration, non-adjacent two of the tubes are extended to the same side, and the remaining two tubes are extended to the opposite side. This configuration reduces the possibility that the user may erroneously connect the tubes.

A second aspect of the flow path switching device according to the present disclosure includes: a body having a first port, a second port, a third port, and a fourth port which are provided at intervals of 90° and capable of being switched between a first state and a second state, the first state being a state in which the first port and the second port are connected and the third port and the fourth port are connected, and the second state being a state in which the first port and the fourth port are connected and the third port and the second port are connected; a first tube connected to the first port, a second tube connected to the second port, a third tube connected to the third port, and a fourth tube connected to the fourth port; and a tube fixing portion that fixes the tubes such that the first tube connected to the first port and the third tube connected to the third port are extended to a same side as viewed in plan and the second tube connected to the second port and the fourth tube connected to the fourth port are extended to a same side, which is an opposite side from the side to which the first tube and the third tube are extended, as viewed in plan.

According to the second aspect of the flow path switching device, non-adjacent two of the tubes are extended to the same side, and the remaining two tubes are extended to the opposite side by the tube fixing portion. This configuration reduces the possibility that the user may erroneously connect the tubes.

The second aspect of the flow path switching device may further include a visual indication portion that visually indicates whether the body is in the first state or the second state. With this configuration, the operator can visually check the switching state. This configuration thus reduces the possibility of erroneous operation.

In the second aspect of the flow path switching device, the tube fixing portion may have a tube holding portion that is independent of the body and that holds the second tube and the third tube such that the second tube and the third tube are extended in opposite directions. With this configuration, the tube fixing portion is implemented by a simple configuration.

In the second aspect of the flow path switching device, the tube fixing portion may be provided on a plate having the body fixed thereto. With this configuration, the tube fixing portion and the body are integrated. The number of components to be used is thus reduced.

In the second aspect of the flow path switching device, the tube fixing portion may include a tube holding portion that holds the second tube and the third tube and a guide projection that guides the second tube and the third tube to the tube holding portion, the tube holding portion and the guide projection being provided on the plate. This configuration reduces or eliminates the possibility of kinking of the tubes.

In the second aspect of the flow path switching device, the tube guide may have a guide projection that is provided between the body and the tube holding portion on a surface of the plate which has the body fixed thereto and that guides the second tube and the third tube to the tube holding portion in a curved manner. The guide projection may include a first projection that is in contact with the second tube and a second projection that is in contact with the third tube. With this configuration, the tubes that are extended to cross each other are less likely to be bent.

In the second aspect of the flow path switching device, the body may include an outer cylinder and a plug, the plug being accommodated in the outer cylinder such that the plug can slide and rotate therein, and the plug having two arc-shaped tunnel-like flow paths independent of each other and each connecting adjacent two of four openings formed at regular intervals in a side surface of the plug, and the plug may be rotatable such that, when the body is in the first state, one of the flow paths connects the first port and the second port and the other flow path connects the third port and the fourth port, and when the body is in the second state, one of the flow paths connects the first port and the fourth port and the other flow path connects the second port and the third port.

With this configuration, the openings formed in the side surface of the plug are connected by the tunnel-like flow paths. This configuration allows a smoother blood flow as compared to the case where grooves or cutouts are formed in the side surface of the plug as flow paths. This configuration also reduces the contact region between the side surface of the plug and blood.

A third aspect of a flow path switching device includes: a body including an outer cylinder and a plug, the outer cylinder having a first port, a second port, a third port, and a fourth port which are provided at regular intervals along its outer circumference, the plug being accommodated in the outer cylinder such that the plug can slide and rotate therein, and the plug having two arc-shaped tunnel-like flow paths independent of each other and each connecting adjacent two of four openings formed at regular intervals in a side surface of the plug. The plug has a recess for visual recognition in its upper surface, and a shape of the flow paths is visually recognizable through the recess for visual recognition.

With this configuration, a visual indication mechanism that allows the operator to visually check the state of the flow paths is easily implemented.

A fourth aspect of a flow path switching device includes: a body including an outer cylinder and a plug, the outer cylinder having a first port, a second port, a third port, and a fourth port which are provided at regular intervals along its outer circumference, the plug being accommodated in the outer cylinder such that the plug can slide and rotate therein, and the plug having two arc-shaped tunnel-like flow paths independent of each other and each connecting adjacent two of four openings formed at regular intervals in a side surface of the plug. The plug has a grip portion with a cross shape in plan which has four protruding portions, and the plug is rotatable between a first position and a second position, the first position being a position in which one of the flow paths connects the first port and the second port and the other flow path connects the third port and the fourth port, and the second position being a position in which one of the flow paths connects the first port and the fourth port and the other flow path connects the second port and the third port. The four protruding portions of the grip portion and the four ports extend in a same direction when the plug is located at the first position and the second position. With this configuration, the operator can intuitively recognize the first position, the second position, and an intermediate position therebetween from the positions of the protruding portions of the grip portion and the positions of the ports.

In each of the above aspects of the flow path switching device of the present disclosure, the first port and the second port may have an indication using a first color, and the third port and the fourth port may have an indication using a second color different from the first color. With this configuration, the operator can easily tell whether connection is in a forward direction or in a reverse direction.

Advantages of the Invention

According to the flow path switching device of the present disclosure, the direction of flow paths in an extracorporeal circuit etc. can be easily switched by a simple operation.

DESCRIPTION OF EMBODIMENTS

Figure 1:
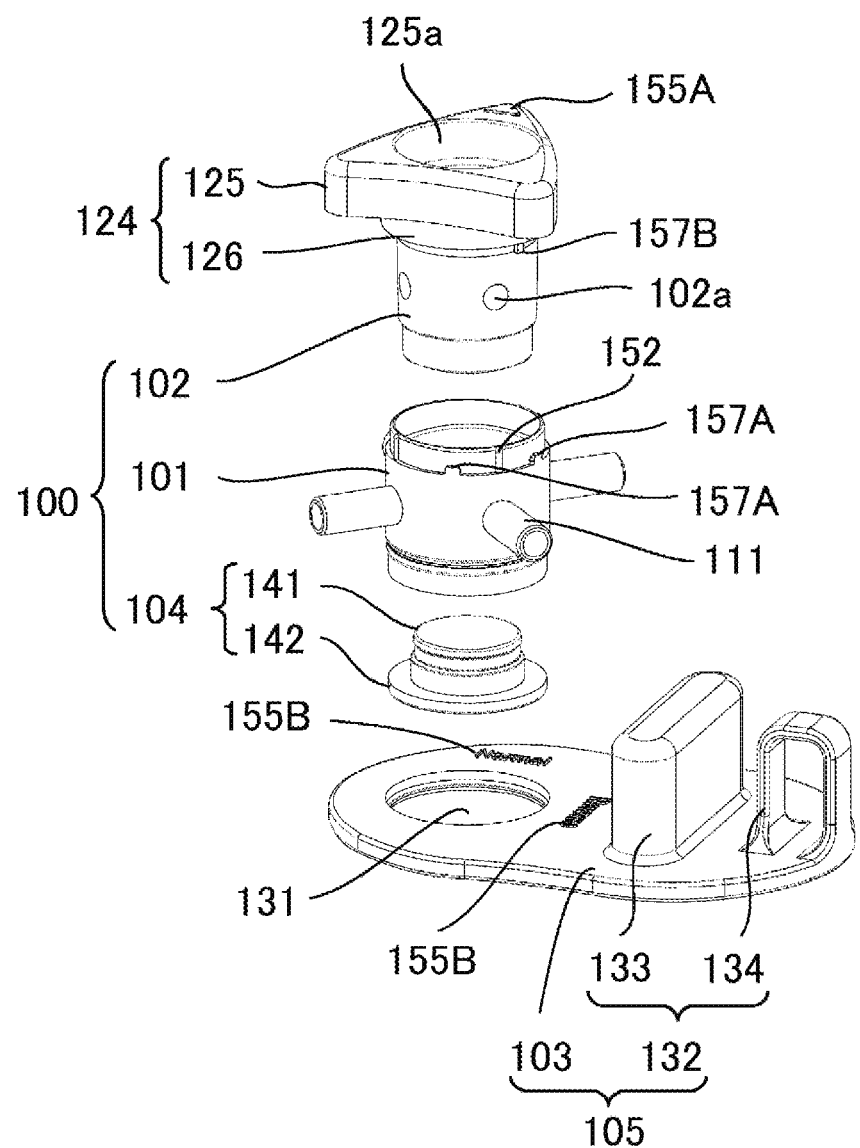
FIG. 1 is an exploded perspective view of a flow path switching device according to an embodiment.
Figure 2:
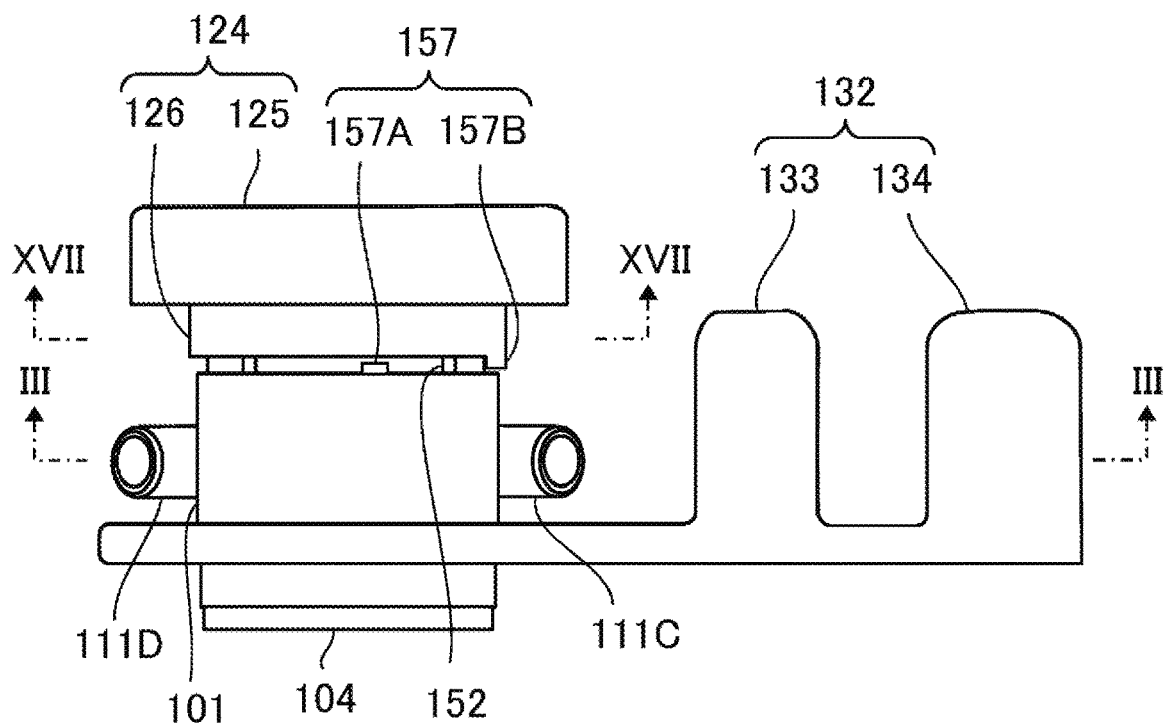
FIG. 2 is a side view of the flow path switching device according to the embodiment.

As shown in FIGS. 1 to 4, a flow path switching device of an embodiment includes a body 100 including an outer cylinder 101, a plug 102, and a retainer 104. The outer cylinder 101 has four ports 111 provided at regular intervals along its outer circumference. Tubes can be connected to the ports 111, and the ports 111 extend through the wall surface of the outer cylinder 101 and is open in the inner wall surface of the outer cylinder 101. The plug 102 has a cylindrical shape, is accommodated in the outer cylinder 101 such that the plug 102 can slide and rotate therein, and has two independent arc-shaped tunnel-like flow paths 121. Each of the two flow paths 121 of the plug 102 connects adjacent two of four openings 102a formed at regular intervals along the outer circumference of the plug 102 so as to correspond to the four ports 111.

In the following description, the flow path switching device of the present embodiment is used with a grip portion 125 side of the plug 102 facing upward. However, the flow path switching device of the present embodiment may be used in any orientation.

The ports 111 of the outer cylinder 101 are provided at every 90 degrees, and the openings 102a of the plug 102 are also formed at every 90 degrees. Accordingly, every time the plug 102 is rotated by 90 degrees, the openings 102a are aligned with the ports 111 and each adjacent two of the ports 111 are connected by the flow paths 121.

Figure 3:
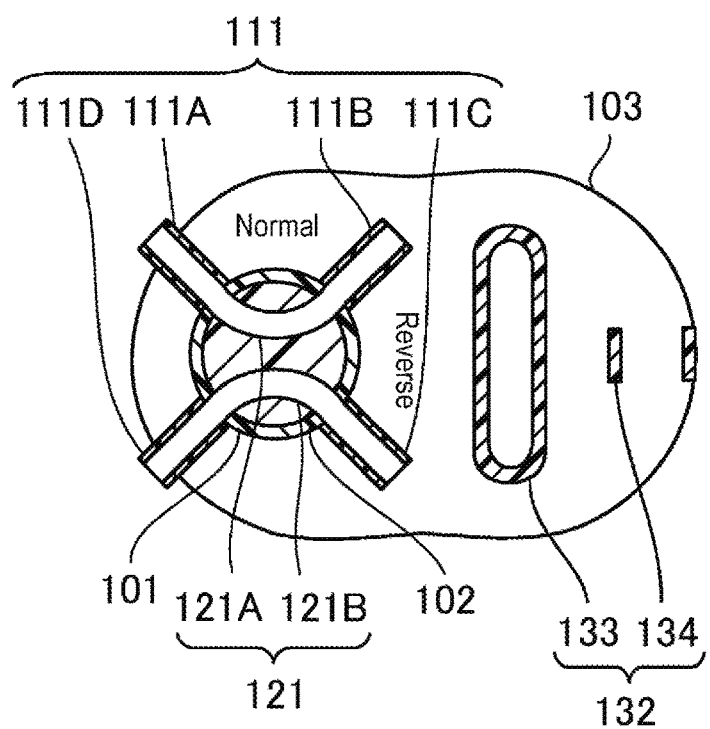
FIG. 3 is a sectional view taken along line in FIG. 2, illustrating the flow path switching device with a plug located at a first position.
Figure 4:
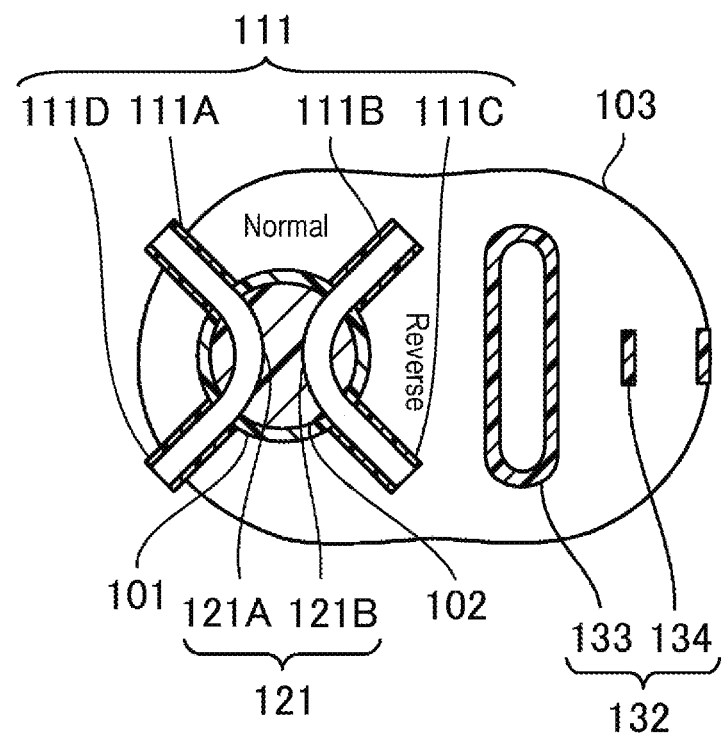
FIG. 4 is a sectional view taken along line in FIG. 2, illustrating the flow path switching device with the plug located at a second position.

Specifically, as shown in FIG. 3, by rotating the plug 102 to a first position, a first port 111A and a second port 111B are connected by a first flow path 121A, and a third port 111C and a fourth port 111D are connected by a second flow path 121B. As shown in FIG. 4, by rotating the plug 102 by 90° from the first position to a second position, the first port 111A and the fourth port 111D are connected by the first flow path 121A, and the third port 111C and the second port 111B are connected by the second flow path 121B.

Figure 5:
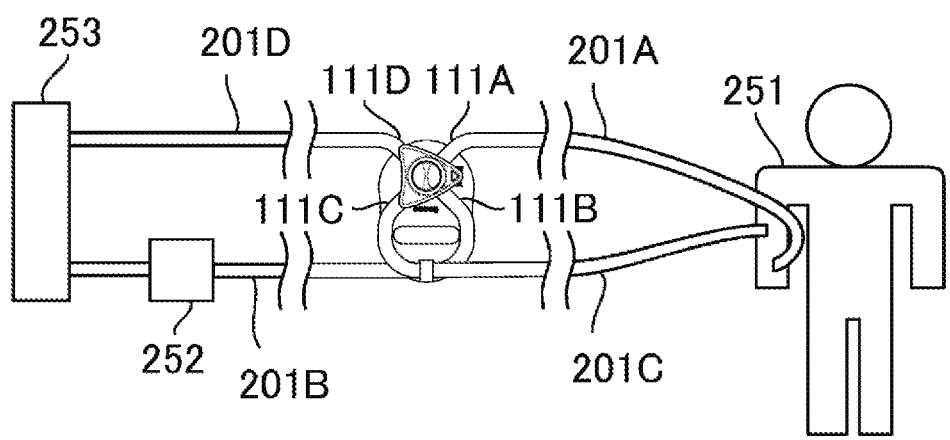
FIG. 5 illustrates an example of use of the flow path switching device.

For example, as shown in FIG. 5, in the flow path switching device of the present embodiment, a first tube (patient-side upstream tube) 201A connected upstream of a vascular access of a patient 251 is connected to the first port 111A, a third tube (patient-side downstream tube) 201C connected downstream of the vascular access of the patient 251 is connected to the third port unit 111C, a second tube (machine-side artery tube) 201B connected to an arterial port of a dialyzer 253 is connected to the second port 111B via a pump 252, and a fourth tube (machine-side vein tube) 201D connected to a venous port of the dialyzer 253 is connected to the fourth port 111D. By rotating the plug 102 to the first position in this state, an extracorporeal circuit in the normal direction is formed in which blood is drawn from upstream of the vascular access and purified blood is returned to downstream of the vascular access. By rotating the plug 102 to the second position, an extracorporeal circuit in the reverse direction is formed in which blood is drawn from downstream of the vascular access and is returned to upstream of the vascular access. The direction of blood flow in extracorporeal circulation can be very easily switched between the normal direction and the reverse direction by using the flow path switching device of the present embodiment.

Each of the flow paths 121 provided in the plug 102 has a tunnel shape connecting adjacent two of the openings 102a and also has an arc shape with no corner. For example, in the case where the tunnel-like flow paths are flow paths (e.g., U-shaped flow paths) each formed by only linear portions (a combination of three linear flow paths) and having a corner (s), blood tends to stagnate in the corner(s), causing coagulation of blood etc. Since the flow paths 121 has an arc shape formed by a curved portion, blood is less likely to stagnate and coagulate therein. The arc shape includes a circular arc shape that is a part of a circle and an elliptical arc shape that is a part of an ellipse. The arc shape also includes a shape formed by two linear portions connected by a curved portion (e.g., U shape).

In order to smoothly connect the flow paths 121 with the ports 111 so as not to form any step that causes blood to stagnate therein, the radius of curvature of the arc-shaped flow path 121 is preferably 3.5 mm or more, more preferably 4.5 mm or more, and preferably 20 mm or less, more preferably 15 mm or less, although it depends on the diameter of the plug 102 and the diameter of the channel that serves as the flow path 121. In order to obtain a sufficient flow rate while reducing the priming volume, the radius of curvature of the arc-shaped flow path 121 is preferably 0.8 times or more, more preferably 0.9 times or more, and preferably 1.2 times or less, more preferably 1.1 times or less, and most preferably 1.0 times the radius of the plug 102. The radius of curvature of the flow path 121 is the radius of curvature of a curve passing through the center of the tunnel-like channel that serves as the flow path 121. When the radius of curvature between the openings 102a is not constant, the radius of curvature of the flow path 121 is the minimum value of the radius of curvature between the openings 102a.

In order for the flow path 121 to connect two of the openings 102a as smoothly as possible so that blood is less likely to stagnate in the flow path 121, it is preferable that the flow path 121 be symmetrical with respect to a straight line connecting the center of the plug 102 and the middle between two of the openings 102a. However, the flow path 121 need not necessarily be symmetrical as long as it has an arc shape.

In the flow path switching device of the present embodiment, the flow paths 121 have a tunnel shape formed in the plug 102. In this case, it is easier to form flow paths with good blood flowability as compared to the case where grooves or cutouts are formed in the surface of the plug 102 as flow paths. For example, it is easy to form flow paths which have a constant sectional area and in which blood is less likely to stagnate locally. The side surface of the plug 102 is present between the flow paths 121 and the inner surface of the outer cylinder 101 except for the positions of the openings 102a. Accordingly, the contact area between the inner surface of the outer cylinder 101 and the side surface of the plug 102 is increased, and a large sealing area is obtained. The outer cylinder 101 appropriately compresses the plug 102, which easily reduces the possibility of blood leakage.

The two flow paths 121 of the plug 102 can be symmetrical with respect to the center of the plug 102. With this configuration, the blood flow is less likely to change when the direction of the flow paths is switched. However, the plug 102 may have two flow paths having different radii of curvature so that the blood flow changes when the direction of the flow paths is switched.

In order to reduce the possibility of blood coagulation, the flow path 121 preferably has a substantially circular section, and particularly preferably has a perfect circular section. Each of the flow paths 121 preferably has a constant sectional area. The tunnel-like flow path 121 having a circular section and a constant sectional area allows blood to more smoothly flow therethrough and further reduces the possibility of blood coagulation etc. However, the flow path 121 may not have a constant sectional area. In order to reduce the possibility that any change may occur when the direction of the flow paths is switched, it is preferable that the two flow paths 121 have the same sectional shape and the same sectional area. However, the two flow paths 121 may have different sectional shapes and different sectional areas from each other.

It is preferable that, at the first position and the second position, the flow paths 121 be connected to the ports 111 with no step therebetween. This configuration further reduces the possibility of blood coagulation in each connection portion between the flow path 121 and the port 111. It is preferable that the tubes 201 connected to the ports 111 have the same sectional area as the flow paths 121. With this configuration, the flow rate and the pressure of blood are less likely to change between the tube 201 and the flow path 121, allowing a smooth blood flow. It is preferable that the flow paths in the ports 111, the tubes 201, and the flow paths 121 have the same sectional area.

The ports 111 may have any configuration as long as the tubes 201 can be connected thereto. For example, the ports 111 may be straight pipes, tapered pipes, etc. on which the tubes 201 can be fitted, or the tubes 201 can be bonded to the ports 111 by solvent bonding etc. The pipes on which the tubes 201 are fitted may have a barbed surface that retains the tubes 201 on the pipes. In the present embodiment, the tubes are undetachably bonded to the ports. However, the ports 111 may be detachable connectors such as lure connectors.

It is preferable that the inside diameter of the outer cylinder 101 be slightly smaller than the outside diameter of the plug 102 so that the plug 102 is compressed by the outer cylinder 101. As the outer cylinder 101 appropriately compresses the plug 102, the possibility of liquid leakage is reduced. Although the plug 102 can be configured so that its entire outer peripheral surface is compressed, the plug 102 may have a portion where the outer peripheral surface is not compressed at a height position where there is no opening in the height direction (axial direction). For example, the plug 102 may be configured so that its intermediate portion where the openings 102a are present is compressed and the plug 102 has a portion that is not compressed in its upper end or lower end other than the intermediate portion. This configuration reduces the possibility of liquid leakage and facilitates rotation of the plug 102.

In order to facilitate rotation of the plug 102 compressed by the outer cylinder 101, it is preferable that either or both of the inner surface of the outer cylinder 101 and the outer surface of the plug 102 be coated with a lubricant or has a lubricating coating. The lubricant or the coating may be a silicon or fluorine lubricant or coating. Either or both of the inner surface of the outer cylinder 101 and the outer surface of the plug 102 may be coated with the lubricant or have the lubricating coating even in the case where the plug 102 is not compressed.

The flow path switching device of the present embodiment has the tunnel-like flow paths and therefore is advantageous in that, even when the inner surface of the outer cylinder 101 and/or the outer surface of the plug 102 is coated with the lubricant etc., blood is less likely to contact the lubricant as compared to the case where the side surface of the plug serves as a flow path.

The material of the outer cylinder 101 and the plug 102 is not particularly limited. For example, the outer cylinder 101 and the plug 102 may be made of polycarbonate, acrylic resin, polyethersulfone, polyethylene, polypropylene, and vinyl chloride. The outer cylinder 101 and the plug 102 may be made of the same material or different materials. In the case where the plug 102 is compressed, the plug 102 may be made of a material that is softer than that of the outer cylinder 101 so that the plug 102 can be more effectively compressed. For example, the plug 102 may be made of a slightly softer material such as vinyl chloride so that the plug 102 can be more effectively compressed and can also slide and rotate smoothly. In order to reduce the possibility of wear of the plug 102, the outer cylinder 101 and the plug 102 may be made of materials having the same hardness.

As shown in FIG. 1, the flow path switching device of the present embodiment has a handle 124 that is integral with the plug 102. The handle 124 has the grip portion 125 and a cover 126 provided below the grip portion 125 and surrounding the upper part of the outer cylinder 101. By gripping and turning the grip portion 125, the plug 102 can smoothly slide and rotate.

The retainer 104 is provided on the opposite side of the outer cylinder 101 from the handle 124 so that the plug 102 does not come off from the outer cylinder 101. In FIG. 1, the retainer 104 has a connection portion 141 connected to the plug 102 and a flange 142 larger than the inside diameter of the outer cylinder 101.

The retainer 104 is provided as needed. For example, the plug 102 may have a claw, a projection, etc. on its lower end so as not to come off from the outer cylinder 101.

The flow path switching device of the present embodiment has a plate 103, and the body 100 is fixed to the plate 103. Providing the plate 103 improves operability of the flow path switching device as the operator can grip the plate 103 when operating the flow path switching device. As will be described later, since the plate 103 has a function to route the tubes 201, the tubes 201 are less likely to be bent etc.

The plate 103 may have a generally rectangular, elliptical, or elongated circular shape in plan with chamfered edges, but the present disclosure is not limited to these shapes. Since the plate 103 has a generally rectangular shape etc. in plan, the body 100 and a tube guide 132 can be effectively arranged thereon. Moreover, since the plate 103 has chamfered edges, the operator or the patient is less likely to feel uncomfortable or be injured when touching the edges. The plate 103 may be narrowed in the middle so that the operator can more easily grip the plate 103.

The body 100 is fixed to the plate 103 by inserting the body 100 into a mount hole 131 formed in the plate 103. Alternatively, the body 100 may be externally threaded and the mount hole 131 may be internally threaded so that the body 100 is screwed into the mount hole 131. However, the present disclosure is not limited to these. The body 100 may be fixed to the plate 103 in any manner. The body 100 may be bonded to the plate 103. In the illustrated example, the body 100 extends through and is fixed to the plate 103. However, the body 100 may not extend through the plate 103.

In the flow path switching device of the present embodiment, as shown in, e.g., FIG. 5, the first tube 201A and the third tube 201C which are connected to the first port 111A and the third port 111C extend toward the patient 251, and the second tube 201B and the fourth tube 201D which are connected to the second port 111B and the fourth port 111D extend toward the dialyzer 253. In this case, the tubes 201 cross each other.

Figure 6:
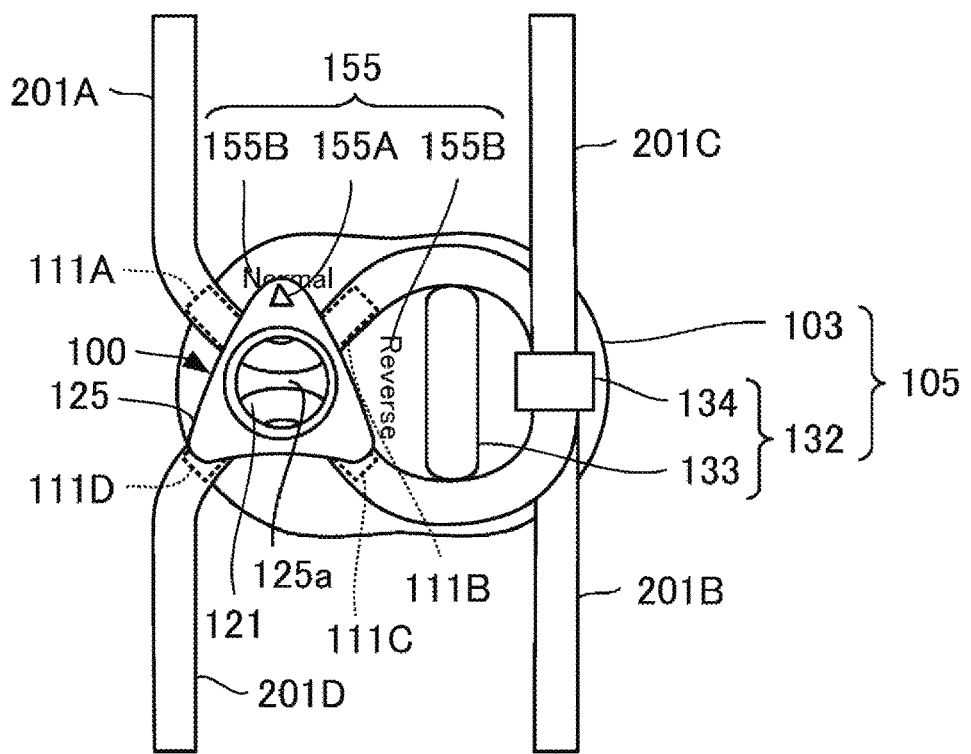
FIG. 6 is a plan view illustrating a tube fixing portion of the flow path switching device according to the embodiment.

The flow path switching device of the present embodiment has a tube fixing portion 105. Two of the tubes 201 which are connected to non-adjacent two of the four ports 111 are thus easily extended to the same side as viewed in plan. In the present embodiment, the body 100 is fixed to the plate 103, and the tube fixing portion 105 has a tube guide 132 on the plate 103. As shown in FIG. 6, the tube guide 132 is configured so that the first tube 201A connected to the first port 111A and the third tube 201C connected to the third port 111C are extended to the same side as viewed in plan, and the second tube 201B connected to the second port 111B and the fourth tube 201D connected to the fourth port 111D are extended to the same side, which is the opposite side from the side to which the first tube 201A and the third tube 201C are extended, as viewed in plan. That is, the second tube 201B and the third tube 201C are fixed so as to cross each other as viewed in plan. This configuration makes it easier to connect the first tube 201A and the third tube 201C to the patient 251 and connect the second tube 201B and the fourth tube 201D to the dialyzer 253 as shown in, e.g., FIG. 5.

The tube guide 132 has a guide projection 133 and a tube holding portion 134. The tube holding portion 134 has a tunnel shape having openings at both ends and is capable of holding two tubes next to each other in the vertical direction. By inserting two of the tubes 201 into the tube holding portion 134 from the opposite openings of the tube holding portion 134, the two tubes 201 can be held in the tube holding portion 134 so as to be extended in opposite directions.

The tube holding portion 134 can be provided at, e.g., an intermediate position between the second port 111B and the third port 111C on the surface (front surface) of the plate 103 which has the body 100 attached thereto. This configuration simplifies the structure of the plate 103. With this structure, the second tube 201B connected to the second port 111B is held so as to extend toward the third port 111C side, and the third tube 201C connected to the third port 111C is held so as to extend toward the second port 111B side. The first tube 201A and the third tube 201C are thus easily extended to the same side, and the second tube 201B and the fourth tube 201D are easily extended to the same side.

The tube holding portion 134 is preferably provided at the intermediate position between the second port 111B and the third port 111C. However, the tube holding portion 134 may be provided at a position offset from the intermediate position as long as it is between the second port 111B and the third port 111C.

The guide projection 133 can be provided between the tube holding portion 134 and the body 100. For example, the guide projection 133 may have a generally rectangular shape in plan and may be parallel to the tube holding portion 134. The longitudinal end faces of the guide projection 133 are curved surfaces that are in contact with the second tube 201B and the third tube 201C and that guide the second tube 201B and the third tube 201C to the tube holding portion 134 in a curved manner.

It is preferable that the curved guide surfaces of the guide projection 133 which guide the second tube 201B and the third tube 201C be located on the outer side in the width direction of the plate 103 with respect to the tip end of the second port 111B and the tip end of the third port 111C. Providing such a guide projection 133 prevents the second tube 201B and the third tube 201C from being bent toward the tube holding portion 134 at a steep angle. However, in the case where the curved guide surfaces are sufficiently far away from the body 100, the curved guide surfaces may be located at positions between the tip ends of the two ports. The tip end side of the port herein refers to the tube side of the port. Since the top surface of the guide projection 133 is located lower than the top surface of the handle 124, the guide projection 133 will not bother the operator when he or she turns the handle 124.

The tube guide 132 is provided as needed. Other configurations may be used as long as the directions of the tubes 201 can be changed so that the tubes 201 are not bent. For example, instead of the tunnel-like tube holding portion 134, two pillars, walls, etc. which sandwich the tubes therebetween may be provided, or two clips, namely upper and lower clips, having a C-shaped section may be provided next to each other in the vertical direction. Any other configuration can be used as long as the two tubes can be held next to each other in the vertical direction. The two tubes may be held next to each other in the horizontal direction rather than being held next to each other in the vertical direction.

In the illustrated example, the guide projection 133 is provided which has a generally rectangular shape in plan. However, a cylindrical or semi-cylindrical guide projection may be provided which has a radius large enough to guide the tubes 201 along the guide projection. In this case, the tube holding portion 134 may be provided which is integral with the side surface of the guide projection.

Figure 7:
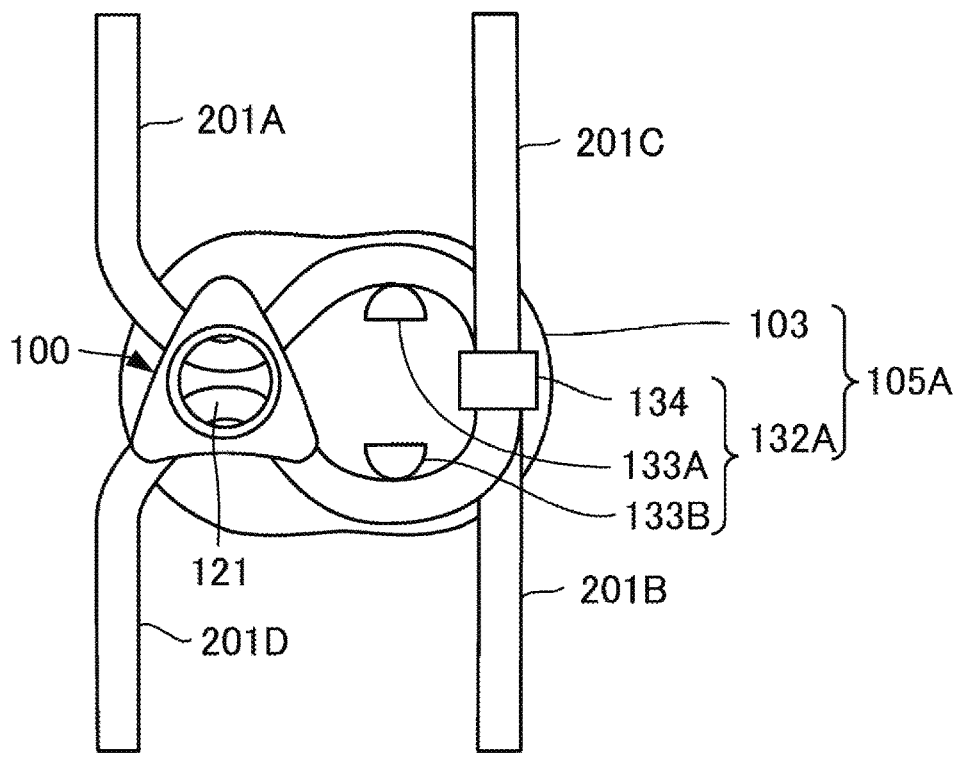
FIG. 7 is a plan view illustrating a tube fixing portion of a flow path switching device according to a first modification.

As in a first modification shown in FIG. 7, a tube fixing portion 105A may include a tube guide 132A having two guide projections 133A, 133B spaced apart from each other. In this case, in order for the tubes not to be bent at a steep angle, it is preferable that the curved guide surface of each guide projection 133A, 133B be located near an imaginary line extended from a corresponding one of the ports.

Two tube holding portions each holding one tube may be provided instead of the guide projections 133A, 133B. For example, as in a second modification shown in FIG. 8, a tube fixing portion 105B may include a tube guide 132B having tube holding portions 134A, 134B, each holding one tube, at the positions of the guide projections 133A, 133B. In this case, it is preferable that the tube holding portion 134A be located on the opposite side of the tip end of the second port 111B from the third port 111C, and the tube holding portion 134B be located on the opposite side of the tip end of the third port 111C from the second port 111B.

Figure 8:
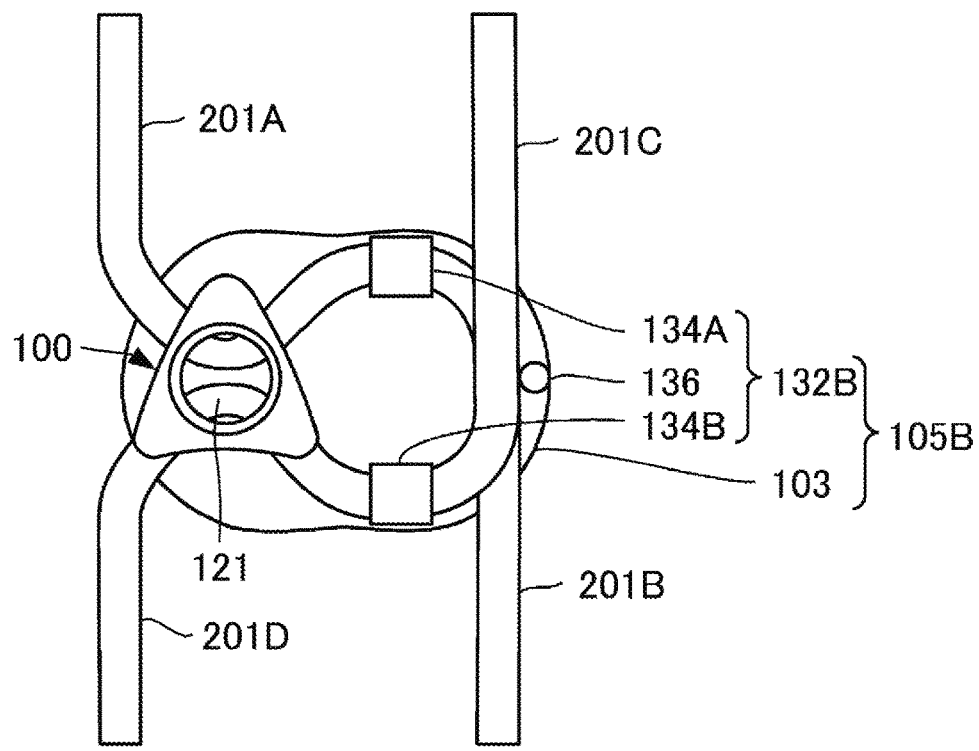
FIG. 8 is a plan view illustrating a tube fixing portion of a flow path switching device according to a second modification.

In FIG. 8, a projection 136 for guiding is provided at a position where the two tubes cross each other. Since the projection 136 is provided, the directions of the tubes can be easily controlled. A tube holding portion that holds the two tubes together may be provided instead of the projection 136. The projection 136 for guiding etc. is provided as needed, and may not be provided depending on the type of tubes etc.

Figure 9:
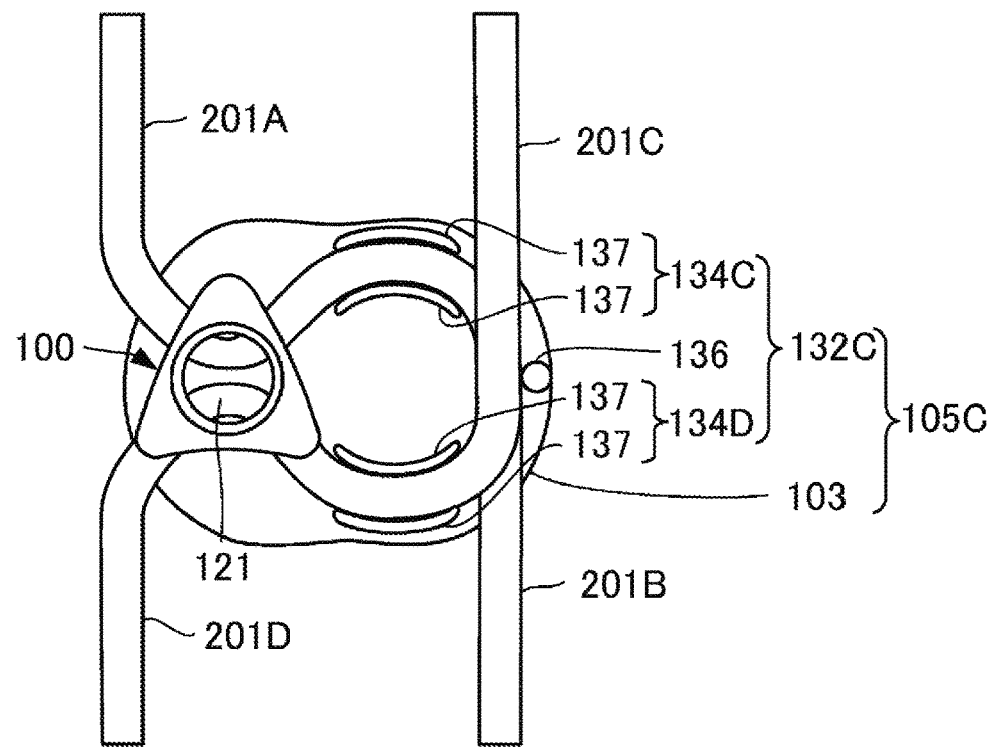
FIG. 9 is a plan view illustrating a tube fixing portion of a flow path switching device according to a third modification.

As in a third modification shown in FIG. 9, a tube fixing portion 105C may include a tube guide 132C having tube holding portions 134C, 134D each formed by two curved walls 137 spaced apart from each other. The interval between the two walls 137 is approximately equal to the outside diameter of the tube. Each of the tube holding portions 134C, 134D sandwiches the tube between the two walls 137 to hold the tube and guides the tube in a predetermined direction along the curve of the walls 137. The walls 137 may not be continuous walls and may be replaced with a plurality of pillars etc.

In FIG. 9, the walls 137 guide the tubes in a curved manner and fix the tubes in such a direction that the tubes cross each other. That is, the walls 137 serve as both a tube holding portion and a guide projection, and the projection 136 may not be provided.

Figure 10:
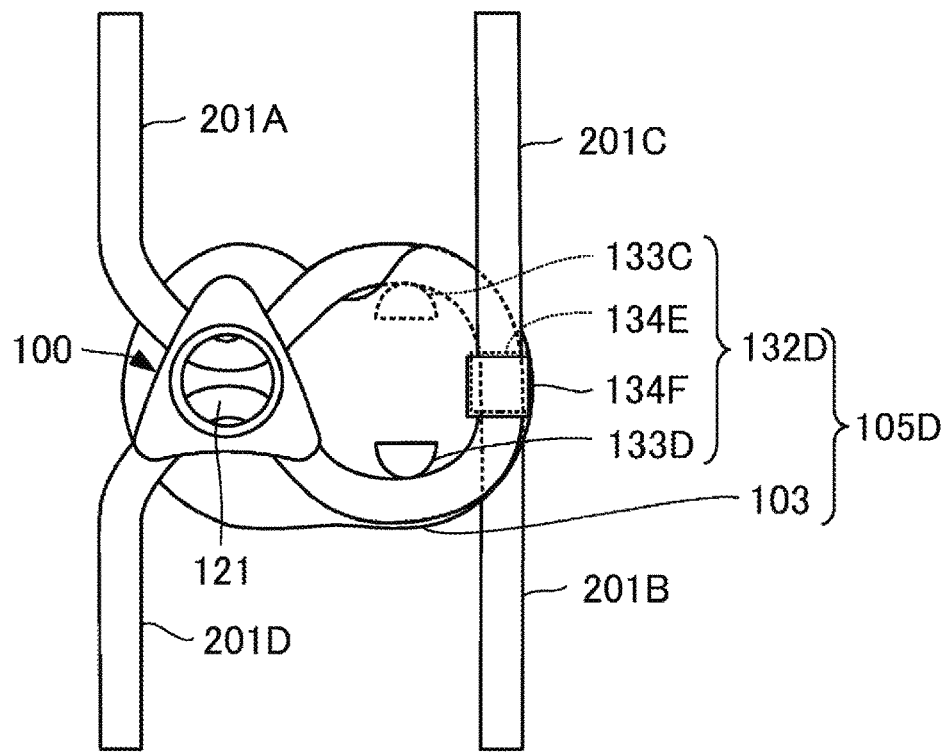
FIG. 10 is a plan view illustrating a tube fixing portion of a flow path switching device according to a fourth modification.

In the illustrated example, the two tubes are held on one surface of the plate 103. However, as in a fourth modification shown in FIG. 10, a tube fixing portion 105D may include a tube guide 132D that holds the two tubes on the opposite sides of the plate 103. In FIG. 10, a guide projection 133C for guiding the second tube 201B and a tube holding portion 134E for holding the second tube 201B are provided on the back surface of the plate 103. A guide projection 133D for guiding the third tube 201C and a tube holding portion 134F for holding the third tube 201C are provided on the front surface of the plate 103. Since the two tubes are placed on the different surfaces of the plate 103, the tubes can be routed more smoothly.

In order to place the tube 201 on the back surface of the plate 103, a recess etc. may be formed in the outer edge of the plate 10 instead of the guide projection so that the tube 201 is guided by the recess. Both of the two tubes may be placed on the back surface of the plate 103. The tube holding portions as in the second modification or the third modification may be used in the fourth modification.

Figure 11:
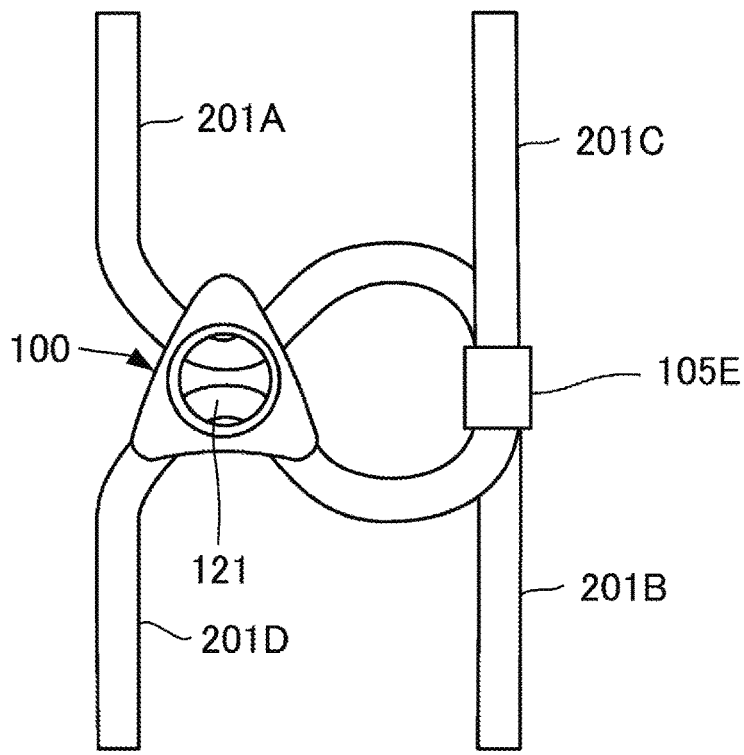
FIG. 11 is a plan view illustrating a tube fixing portion of a flow path switching device according to a fifth modification.

In the illustrated example, the tube fixing portion 105 has the tube guide 132 fixed to the plate 103. However, a tube guide that is independent of the body 100 and is not fixed to the plate 103 may be used. For example, a tube fixing portion 105E in a fifth modification shown in FIG. 11 holds the two tubes together and guides them so that they are extended in opposite directions. However, there is no plate and the tube fixing portion 105E is independent of the body 100. In this configuration, the tubes support each other. The tubes are therefore less likely to be bent even though they are not fixed to the plate. For example, the tube fixing portion 105E may be a hollow cylindrical member through which the two tubes can be passed. However, the present disclosure is not limited to this, and the tube fixing portion 105E may have any configuration as long as it can hold the two tubes together such that they are extended in opposite directions.

Figure 12:
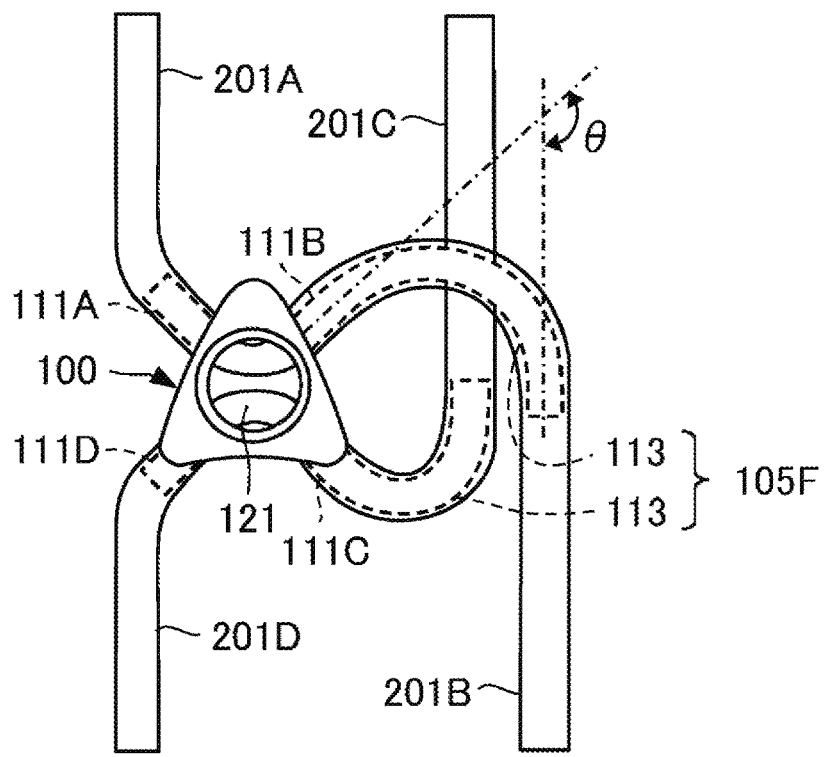
FIG. 12 is a plan view illustrating a tube fixing portion of a flow path switching device according to a sixth modification.

The tube fixing portion is illustrated which guides the tubes connected to the ports and extend the tubes in predetermined directions. However, as shown in a sixth modification shown in FIG. 12, a tube fixing portion 105F may have direction changing portions 113 each changing the direction of the port. In this configuration, since the body 100 functions as a tube fixing portion that defines the directions in which the tubes are extended, the tube fixing portion 105F is not independent of the body 100. In FIG. 12, each of the second port 201A and the third port 111C is provided with the direction changing portion 113. The direction changing portions 113 change the directions in which the second port 111B and the third port 111C extend. The first tube 201A and the third tube 201C are extended in the same direction as viewed in plan, and the second tube 201B and the fourth tube 201D are extended in the same direction as viewed in plan.

In order to extend the tubes connected to the ports located on the opposite sides of the body 100 in the same direction as viewed in plan, it is preferable that each of the direction changing portions 113 change the direction in which the port extends by an angle θ of 135 degrees. Since the tubes are flexible, the angle θ may be 135 degrees or less and is preferably 60 degrees or more, more preferably 90 degrees or more, and even more preferably 120 degrees or more. The angle θ may be larger than 135 degrees and is preferably 145 degrees or less. The angle θ may be about 180 degrees in order to extend the two tubes parallel to each other. In order to avoid blood coagulation in the direction changing portions 113, it is preferable that the cavity of each of the direction changing portions 113 have a shape with no corner.

In order to reduce the possibility that blood may stagnate in the direction changing portions 113, it is preferable that the cavity of each of the direction changing portions 113 be connected to the cavity of a corresponding one of the ports 111 with no step therebetween. It is therefore preferable that the direction changing portion 113 be integral with the port 111. However, the direction changing portion 113 and the port 111 may be molded separately and put together.

Figure 13:
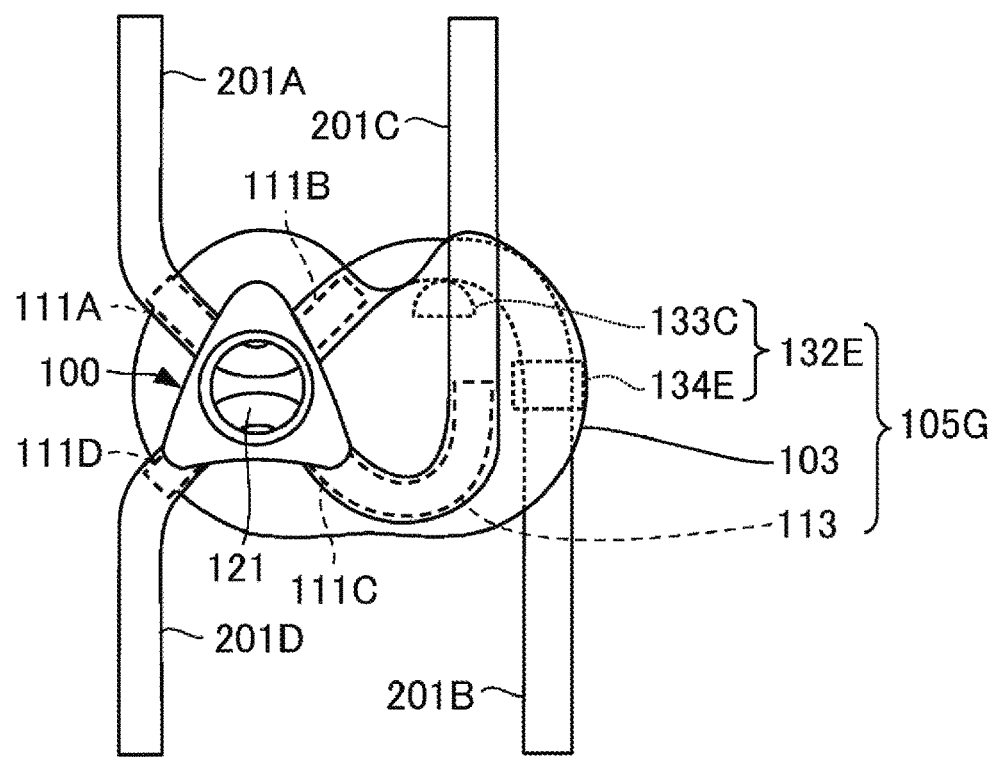
FIG. 13 is a plan view illustrating a tube fixing portion of a flow path switching device according to a seventh modification.

In the illustrated example, the direction changing portions 113 are connected to the second port 111B and the third port 111C. However, the direction changing portion 113 may be connected to only one of the two ports, and the tube guide may change the direction in which the tube connected to the other port is extended. For example, as in a seventh modification shown in FIG. 13, a tube fixing portion 105G has the direction changing portion 113 connected to the third port 111C and a tube guide 132E. The tube guide 132E has the guide projection 133C and the tube holding portion 134E which are provided on the back surface of the plate 103, and the second tube 201B is extended in the opposite direction to that in which the third tube 201C is extended.

The tube guide 132E is not limited to this configuration and may have other configuration as long as it can guide one tube. For example, the tube guide 132E may be provided on the front surface of the plate 103. The direction changing portion 113 may be bent not only in the horizontal direction but also in the vertical direction so that the end of the direction changing portion 113 reaches the back side of the plate 103.

In the illustrated example, the tube fixing portion changes the directions in which the second tube 201B and the third tube 201C are extended. However, the tube fixing portion may change the directions in which the first tube 201A and the fourth tube 201D are extended.

It is preferable that the flow path switching device of the present embodiment have an operation assist mechanism that makes the user aware that the plug 102 is located at the first position or the second position. For example, the operation assist mechanism may be a visual indication mechanism that makes the user visually aware that the plug 102 is located at the first position or the second position.

Figure 14:
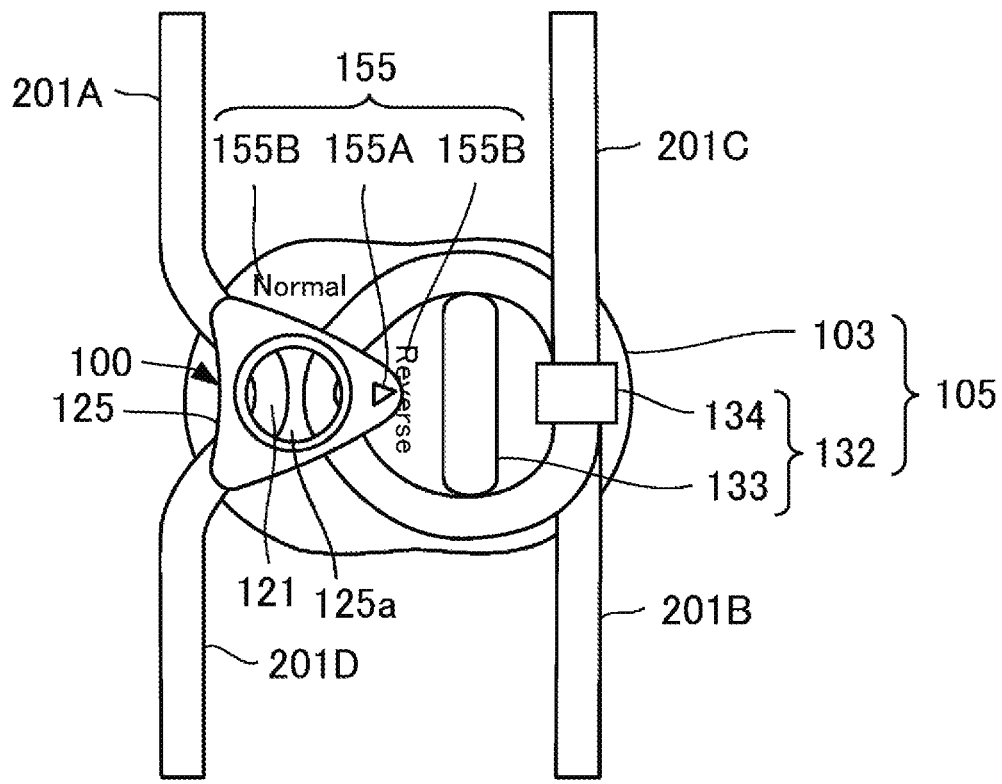
FIG. 14 is a plan view illustrating a flow path switching device with a plug located at the second position.

As shown in, e.g., FIGS. 6 and 14, a visual indication mechanism 155 may be visual indicators 155A, 155B provided on the grip portion 125 for rotating the plug 102 and the plate 103. In the example illustrated in FIGS. 6 and 14, the indicator 155A is a symbol and the indicators 155B are characters. However, various visual indications such as symbols, characters, and colors may be combined as desired. In FIGS. 6 and 14, the indicators 155B are provided on the plate 103 having the outer cylinder 101 attached thereto. However, the indicators 155B may be provided at other positions if the position of the plug 102 can be specified. The indicator 155A may be provided at a position other than on the grip portion 125.

As the visual indication mechanism, the plug 102 including the grip portion 125 may have a reduced thickness, namely the plug 102 including the grip portion 125 may have a recess 125a for visual recognition in the center, so that the user can visually recognize the flow paths 121 in the plug 102 from the outside. The entire recess 125a other than on the flow paths 121 in the plug 102 is made deeper so that the flow paths 121 look raised when the user look at the flow paths 121 through the recess 125a. With this configuration, the recess 125a can be used as the visual indication mechanism, that is, the operation assist mechanism, which allows the user to tell the directions of the flow paths 121, namely whether the plug 102 is currently located at the first position, the second position, or an intermediate position therebetween. The flow path switching device may be configured so that the user can visually recognize blood flowing through the flow paths 121 in the plug 102. The plug 102 and the handle 124 may be transparent or translucent in order that the user can visually recognize the flow paths 121. The flow path switching device configured so that the user can visually recognize blood flowing through the flow paths 121 is also advantageous in that it is easier to check if air bubbles in the flow paths 121 have been removed.

The flow path switching device may be configured so that the user can visually recognize blood flowing through the flow paths 121 in the plug 102. The plug 102 and the handle 124 may be transparent or translucent in order that the user can visually recognize the flow paths 121. The recess 125a may not be provided in the case where the plug 102 and the handle 124 is transparent or translucent. The flow path switching device configured so that the user can visually recognize blood flowing through the flow paths 121 is also advantageous in that it is easier to check if air bubbles in the flow paths 121 have been removed.

The retainer 104 side of the plug 102 may be made thinner so that the user can visually recognize blood in the flow paths 121 from the retainer 104 side as well. In the case where the retainer 104 and the plug 102 are fixed so that they cannot rotate relative to each other, a recess similar to that of the grip portion 125 may be formed in the retainer 104 so that the user can visually recognize blood in the flow paths 121 from the retainer 104 side as well. With this configuration, the user can check the positions of the flow paths 121 from both the retainer 104 side and the grip portion 125 side. An indication of the directions of the flow paths 121 may be provided instead of the user being able to directly visually recognize blood in the flow paths 121 from the retainer 104 side.

Figure 15:
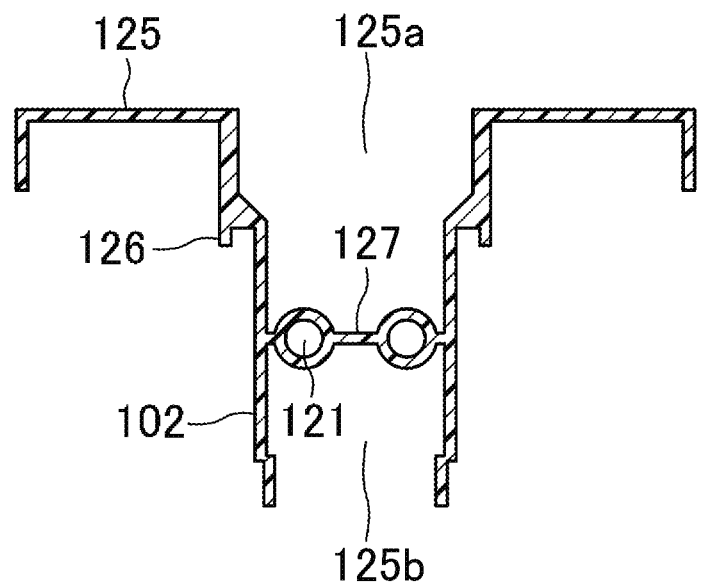
FIG. 15 is a sectional view of the plug.

For example, as shown in FIG. 15, the plug 102 may have a hollow cylindrical shape having a partition wall 127 in its intermediate portion where the flow paths 121 are provided. The portions of the partition wall 127 which correspond to the flow paths 121 are made thicker than the remaining portion of the partition wall 127. Outer walls having a shape corresponding to that of the flow paths 121 are thus formed around the flow paths 121. With this configuration, the user can visually recognize the shape of the flow paths 121 from the outside. The flow paths 121 can thus be used as the visual indication mechanism.

Since the plug 102 has a hollow cylindrical shape having the partition wall 127 in its intermediate portion, the recess 125a for visual recognition is formed in the upper surface side where the grip portion 125 is provided, and a recess 125b for visual recognition is formed in the back surface side where the retainer 104 is provided. However, in the case where it is not necessary to visually recognize the flow paths 121 from the back side, the recess 125b may not be provided on the back side.

The thickness of the outer wall of the flow path 121 can be determined in view of the inside diameter of the flow path 121, the pressure that is applied to the flow path 121, the material of the plug 102, etc., but is usually about 0.5 mm to 2 mm.

The larger the diameter of the recess 125a for visual recognition is, the better the visibility of the flow paths 121 is. In FIG. 15, the diameter of the recess 125a is larger on the side farther from the flow paths 121 than on the side closer to the flow paths 121. This configuration further improves the visibility of the flow paths 121. The partition wall 127 may also have depressions between the wall surface of the plug 102 and the flow paths 121. This configuration further improves the visibility of the shape of the flow paths 121.

The recess 125a for visual recognition may have any shape as long as the user can visually recognize the flow paths 121. The shape of the recess 125a is not limited to a circle in plan, and may be a polygon such as a quadrilateral in plan.

In FIGS. 6 and 14, the grip portion 125 has a generally triangular shape in plan. Since the grip portion 125 has a planar shape that does not have rotational symmetry after a 90° rotation, the grip portion 125 itself may be used as a visual indication for the operation assist mechanism. The grip portion 125 having a generally triangular shape etc. is also advantageous in that the grip portion 125 is easier to grip as compared to the case where the grip portion 125 has a circular shape in plan. The grip portion 125 may have curved sides or may have chamfered edges. This further improve operability etc. The grip portion 125 may have an anti-slip rib(s) etc. on its side surface.

Figure 16:
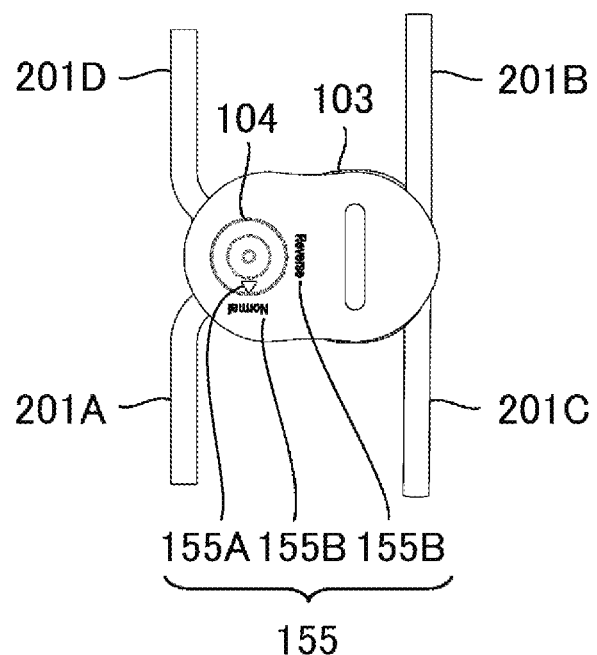
FIG. 16 is a bottom view illustrating a flow path switching device with a plug located at the first position.

In the illustrated example, the visual indication is provided on the upper side where the handle 124 is provided. However, as shown in FIG. 16, the visual indication mechanism 155 may also be provided on the lower side where the retainer 104 is provided. With this configuration, the user can check the condition of the flow paths from both sides, and the operability is further improved. A grip portion for rotating the plug 102 may also be provided on the retainer 104 side. With this configuration, the user can perform the operation of switching the flow path from both sides.

The flow path switching device according to the present embodiment may include a click mechanism that makes the user aware that the plug 102 is located at the first position or the second position.

Figure 17:
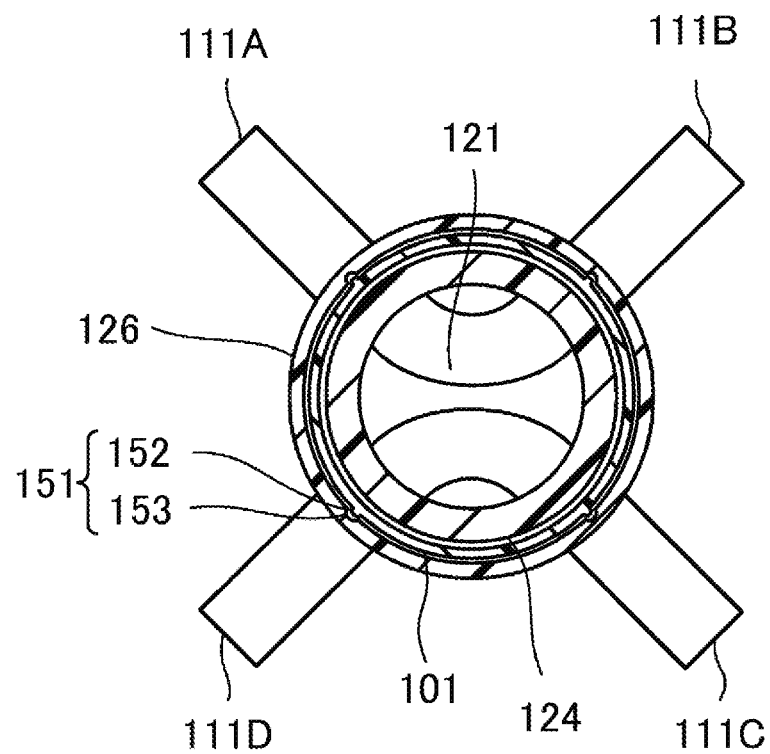
FIG. 17 is a sectional view taken along line XVII-XVII in FIG. 2, illustrating the flow path switching device with the plug located at the first position.

For example, a click mechanism 151 may be composed of protrusions 152 formed on the outer surface of the upper part of the outer cylinder 101 and recesses 153 formed in the inner surface of the cover 126 of the handle 124. As shown in FIG. 17, the protrusions 152 and the recesses 153 may be formed so that the protrusions 152 engage with the recesses 153 when the plug 102 reaches the second position while the user is rotating the plug 102 from the first position toward the second position and when the plug 102 reaches the first position while the user is rotating the plug 102 from the second position toward the first position. When the protrusions 152 engage with the recesses 153, resistance to rotation of the plug 102 occurs, giving the user who is gripping the handle 124 the feel of a click.

In the example illustrated in FIG. 17, each of the protrusion 152 and the recess 153 is formed at four positions. However, forming one of the protrusion 152 and the recess 153 at a minimum of one position and the other at a minimum of two positions gives the user the feel of clip stops at the first and second positions. A recess(es) may be formed in the outer cylinder 101 and a protrusion(s) may be formed on the handle 124. A protrusion(s) may be formed on both the outer cylinder 101 and the handle 124 so that the protrusions on the outer cylinder 101 and the handle 124 get over each other. The protrusions 152 and the recesses 153 may be formed in a part of the plug 102 which is not compressed by the outer cylinder 101.

The flow path switching device of the present embodiment may include a rotation restriction mechanism 157 that restricts the rotation range of the plug 102 to up to 90° between the first position and the second position. In FIG. 1, the rotation restriction mechanism 157 is composed of rotation restriction protrusions 157A, 157B formed on the outer surface of the upper part of the outer cylinder 101 and the cover 126 of the handle 124. The handle 124 and the plug 102 connected thereto are not allowed to rotate beyond the position where the rotation restriction protrusions 157A, 157B contact each other. The present disclosure is not limited to this, and any configuration may be used as long as the rotation range of the plug 102 can be restricted to a predetermined range. Since rotation of the plug 102 stops at the first position or the second position due to the rotation restriction mechanism 157, this makes the user aware that the plug 102 has reached the first position or the second position. Accordingly, providing the rotation restriction mechanism 157 facilitates the switching operation. The rotation restriction mechanism may allow the plug 102 to rotate to up the position of 180°, up to the position of 270°, or up to the position of 360° or may not restrict rotation of the plug 102.

These operation assist mechanisms are provided as needed, and one or more types of operation assist mechanisms can be combined as desired. For example, providing the click mechanism, the visual indication mechanism, and the rotation restriction mechanism reduces the possibility of erroneous operation as there are a plurality of ways that make the user aware that the direction of the flow paths has been switched.

The outer cylinder 101, the plug 102, the plate 103, and the retainer 104 may be resin moldings. For example, the outer cylinder 101, the plug 102, the plate 103, and the retainer 104 may be molded of polyethylene, polypropylene, polycarbonate, acrylonitrile-butadiene-styrene copolymer, acrylic resin, polyethersulfone, etc. The outer cylinder 101, the plug 102, the plate 103, and the retainer 104 may be made of the same material or different materials. The plug 102 and the handle 124 may be molded as a single-piece member, or may be separately molded and then put together. The outer shape of the outer cylinder 101 is not limited to a circle in plan and may be any shape. For example, the outer shape of the outer cylinder 101 may be a quadrilateral in plan.

The plate 103 together with the tube guide may be formed as a single-piece member. The guide projection may be molded as a hollow projection depending on its size. In this case, the plate having the guide projection is easily molded, and the amount of resin material required is reduced. The tube guide may be molded separately from the plate 103 and the tube guide and the plate 103 may then be put together.

In the illustrated example, the flow path switching device has the grip portion with a generally triangular shape in plan. However, like a flow path switching device of the seventh modification shown in FIGS. 18 to 20, the flow path switching device may have a grip portion 325 with a generally cross shape in plan which has four protruding portions 328. In the case where the grip portion 325 has a cross shape, the number of protruding portions of the grip portion 325 is the same as that of ports 311. In this case, the flow path switching device can be configured so that the four protruding portions 328 of the grip portion 325 and the four ports 311 extend in the same direction and overlap each other as viewed in plan when a plug 302 is located at the first position or the second position. With this configuration, the user can easily visually verify completion of the switching. Moreover, the user can easily tell that the protruding portions 328 of the grip portion 325 and the ports 311 extend in the same direction not only when looking at the flow path switching device in plan but also when looking at the flow path switching device from the side. The user can therefore easily visually verify completion of the switching even in the case where he or she operates the flow path switching device disposed transversely. Moreover, the user can tell that the protruding portions 328 and the ports 311 extend in the same direction not only visually but by touching with hand.

Indicators 355A are provided on the protruding portions 328 of the grip portion 325. This allows the user to more visually recognize the position of the plug 302. An indicator is provided on the port 311. This allows the user to more visually recognize the directions of flow paths 321. For example, the ports 311 that are located on the artery side when the plug 302 is at the first position have an indication using a first color, which is red, and the ports 311 that are located on the vein side when the plug 302 is located at the first position have an indication using a second color, which is blue. A visual indication of the directions of the flow paths 321 may be provided on the plug 302. This allows the user to instantly recognize by the visual indication on the plug 302 that the ports 311 having the red indication are connected to each other and the ports 311 having the blue indication are connected to each other when the plug 302 is at the first position, and also allows the user to instantly recognize that the ports 311 having the red indication are connected to the ports 311 having the blue indication when the plug 302 is at the second position. The use can easily visually tell whether the direction of the flow path is the forward direction or in the reverse direction.

For example, the indication of the directions of the flow paths 321 which is provided on the plug 302 is a recess 325a for visual recognition which allows the user to visually recognize the shape of the flow paths 321. However, the present disclosure is not limited to this, and any indication may be used as long as it shows the directions of the flow paths 321.

For example, the ports 311 may have the color indications as follows. In the case where the tubes are directly connected to the ports 311, colored hollow cylindrical cover members are fitted on the ports or the tubes. Alternatively, the tubes or the ports 311 themselves or the regions around the tubes or the ports 311 may have the color indications. For example, colored tape may be attached to the surfaces of the tubes, or color indications may be engraved, printed, etc. on the surfaces of the tubes. The ports 311 may be connected with the tubes using colored connectors. The present disclosure is not limited to the color indications, and characters or symbols may be used, or a combination of two or more of colors, characters, and symbols may be used. The flow path switching device having a generally triangular shape in plan may have similar indications.

The flow path switching device of this modification has a block-like back-side grip portion 303 on the opposite side of an outer cylinder 301 from the grip portion 325. With this configuration, the user can grip the grip portion 325 with one hand and the back-side grip portion 303 with the other hand. The user can thus easily rotate the plug 302. This configuration not only allows the user to easily grip the grip portions but also achieves reduction in size of the flow path switching device. The back-side grip portion 303 has the shape of a quadrilateral prism. Aligning the corners of the back-side grip portion 303 with the positions of the ports 311 not only allows the user to easily grip the grip portions but also achieves reduction in size. The planar shape of the back-side grip portion 303 is not limited to the quadrilateral and may be, e.g., a circle, a triangle, a hexagon, etc. However, the back-side grip portion 303 having a shape with corners is easier to grip.

Figure 18:
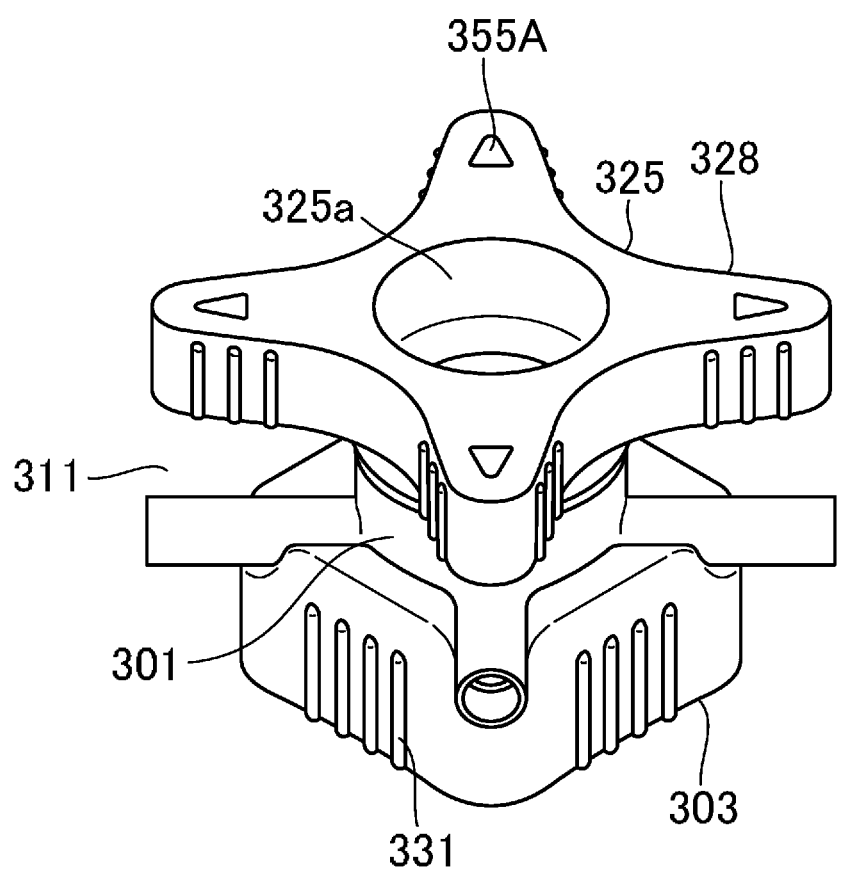
FIG. 18 is a perspective view of a flow path switching device according to a seventh modification.
Figure 19:
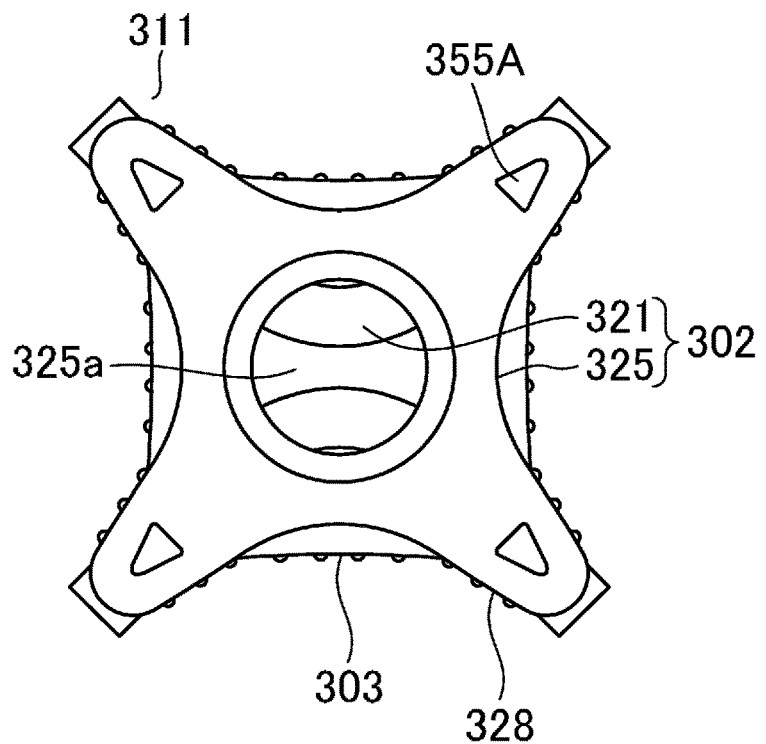
FIG. 19 is a plan view of the flow path switching device according to the seventh modification with a plug located at the first position.
Figure 20:
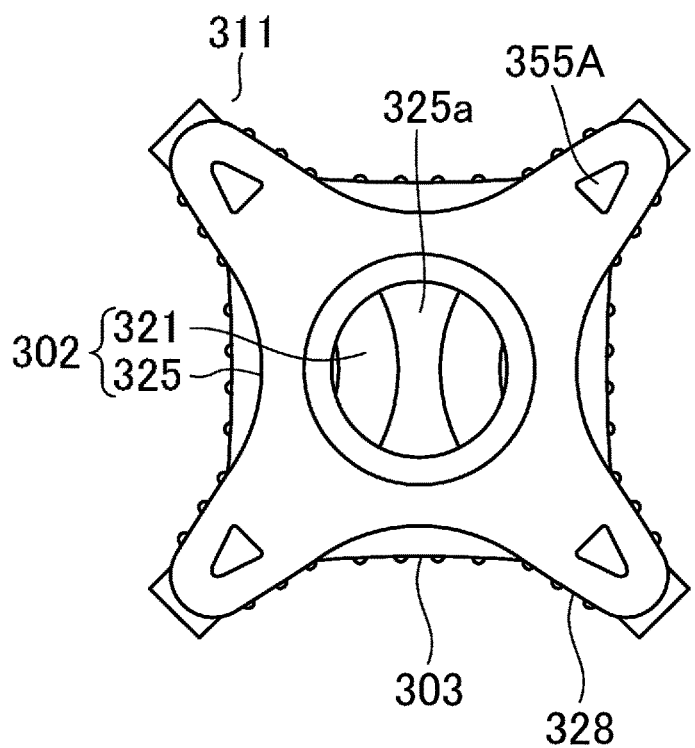
FIG. 20 is a plan view of the flow path switching device according to the seventh modification with the plug located at the second position.

In FIGS. 18 to 20, the back-side grip portion 303 has a plurality of anti-slip ribs 331 on its side surface. The side surface of the back-side grip portion 303 is wide enough that the user can place his or her fingers thereon. Specifically, the side surface of the back-side grip portion 303 is wider than the side surface of the grip portion 325. Accordingly, with the side surface of the back-side grip portion 303 facing toward the user, the user can place fingers (e.g., thumb and index finger) on the ribs 331 and firmly hold the back-side grip portion 303 with fingers. The user can also grip the grip portion 325 with the other hand and easily rotate the grip portion 325 relative to the back-side grip portion 303. The means for making it easier to grip the grip portion with fingers is not limited to the ribs, and may be a recess that catches a finger.

In order that the user can easily rotate the plug 302, it is preferable that the flow path switching device of this modification separately have such a tube fixing portion as illustrated in the fifth modification which hold the two tubes together and guides them so that they are extended in opposite directions. The flow path switching device of this modification may have such direction changing portions as illustrated in the sixth modification which change the directions of the ports. The flow path switching device of this modification may have a plate having a tube fixing portion, instead of the back-side grip portion.

As in the embodiment and the other modifications, the flow path switching device of this modification may include a click mechanism that makes the user aware that the plug 302 is located at the first position or the second position, or a rotation restriction mechanism that restricts the rotation range of the plug 302.

In the flow path switching devices of the embodiment and the modifications, the direction in which each port extends can be changed according to the purpose of use. For example, in view of the fact that either the two ports 111D, 111B or the two ports 111A, 111C are on the patient side and the other two ports 111D, 111B or 111A, 111C are on the dialyzer side, the angle between the ports 111D, 111B and the angle between the ports 111A, 111C may be reduced. For example, the ports may be formed so that the ports 111A, 111D are coaxial in order to clearly indicate appropriate orientations of the patient, the dialyzer and the flow path switching device to the user.

INDUSTRIAL APPLICABILITY

The flow path switching device of the present disclosure is easy to operate and is useful as a flow path switching device for a blood circuit etc.

DESCRIPTION OF REFERENCE CHARACTERS

100 Body
101 Outer Cylinder

102 Plug
102a Opening
103 Plate
104 Retainer
105 Tube Fixing Portion
105A Tube Fixing Portion
105B Tube Fixing Portion
105C Tube Fixing Portion
105D Tube Fixing Portion
105E Tube Fixing Portion
105F Tube Fixing Portion
105G Tube Fixing Portion
111 Port
111A First Port
111B Second Port
111C Third Port
111D Fourth Port
113 Direction Changing Portion
121 Flow Path
121A First Flow Path
121B Second Flow Path
124 Handle
124a Recess
125 Grip Portion
125a Recess for Visual Recognition
125b Recess for Visual Recognition
126 Cover
127 Partition Wall
131 Mount Hole
132 Tube Guide
132A Tube Guide
132B Tube Guide
132C Tube Guide
132D Tube Guide
132E Tube Guide
133 Guide Projection
133A Guide Projection
133B Guide Projection
133C Guide Projection
133D Guide Projection
134 Tube Holding Portion
134A Tube Holding Portion
134B Tube Holding Portion
134C Tube Holding Portion
134D Tube Holding Portion
134E Tube Holding Portion
134F Tube Holding Portion
136 Projection
137 Wall
141 Connection Portion
142 Flange
151 Click Mechanism
152 Protrusion
153 Recess
155 Visual Indication Mechanism
155A Indicator
155B Indicator
157 Rotation Restriction Mechanism
157A Rotation Restriction Protrusion
157B Rotation Restriction Protrusion
201 Tube
201A First Tube
201B Second Tube
201C Third Tube
201D Fourth Tube
251 Patient
252 Pump
253 Dialyzer
301 Outer Cylinder
302 Plug
303 Back-Side Grip Portion
311 Port
321 Flow Path
325 Grip Portion
325a Recess for Visual Recognition
328 Protruding Portion
331 Rib
355A Indicator

The invention claimed is:

1. A flow path switching device, comprising:
a body having a first port, a second port, a third port, and a fourth port which are provided at intervals of 90° and capable of being switched between a first state and a second state, the first state being a state in which the first port and the second port are connected and the third port and the fourth port are connected, and the second state being a state in which the first port and the fourth port are connected and the third port and the second port are connected;
a tube fixing portion configured to change directions in which at least part of the tubes are extended, and fix the tubes to hold the directions, wherein
a first tube connected to the first port, a second tube connected to the second port, a third tube connected to the third port, and a fourth tube connected to the fourth port; and
the tube fixing portion that fixes the tubes such that the first tube connected to the first port and the third tube connected to the third port are extended to a same side as viewed in plan and the second tube connected to the second port and the fourth tube connected to the fourth port are extended to a same side, which is an opposite side from the side to which the first tube and the third tube are extended, as viewed in plan, and
the tube fixing portion has one of following configurations:
a first tube holding portion that holds the second tube and the third tube to cross each other and a guide projection that guides the second tube and the third tube to the tube holding portion, the tube holding portion and the guide projection being provided on a plate having the body fixed thereto,
a second tube holding portion that is independent of the body and that holds the second tube and the third tube together such that the second tube and the third tube are extended in opposite directions, or
two of direction changing elements that provide with the second port and the third port and that guide the second tube and the third tube so that they are extended in opposite directions.

2. The flow path switching device according to claim 1, further comprising:
a visual indication portion that visually indicates whether the body is in the first state or the second state.

3. The flow path switching device according to claim 1, wherein
the tube fixing portion has the second tube holding portion that is independent of the body and that holds the second tube and the third tube such that the second tube and the third tube are extended in opposite directions.

4. The flow path switching device according to claim 1, wherein
the body includes an outer cylinder and a plug, the plug being accommodated in the outer cylinder such that the plug can slide and rotate therein, and the plug having two arc-shaped tunnel-like flow paths independent of each other and each connecting adjacent two of four openings formed at regular intervals in a side surface of the plug, and the plug is rotatable such that, when the body is in the first state, one of the flow paths connects the first port and the second port and the other flow path connects the third port and the fourth port, and when the body is in the second state, one of the flow paths connects the first port and the fourth port and the other flow path connects the second port and the third port.

5. A flow path switching device, comprising:

a body including an outer cylinder and a plug, the outer cylinder having a first port, a second port, a third port, and a fourth port which are provided at regular intervals along its outer circumference, the plug being accommodated in the outer cylinder such that the plug can slide and rotate therein, and the plug having two flow paths independent of each other and each connecting adjacent two of four openings formed at regular intervals in a side surface of the plug, wherein the plug has a recess for visual recognition in its upper surface exposed to the outside of the outer cylinder, a bottom of the recess for visual recognition has two raised portions corresponding to positions of the two flow paths and a groove provided between the two raised portions, and the two raised portions and the groove are visually recognizable through the recess for visual recognition so that the two flow paths look raised and functions as an indicator indicating which one of the second port and the third port the first port connects to and which one of the second port and the third port the fourth port connects to.

6. A flow path switching device, comprising:

a body including an outer cylinder and a plug, the outer cylinder having a first port, a second port, a third port, and a fourth port which are provided at regular intervals along its outer circumference, the plug being accommodated in the outer cylinder such that the plug can slide and rotate therein, and the plug having two arc-shaped tunnel-like flow paths independent of each other and each connecting adjacent two of four openings formed at regular intervals in a side surface of the plug, wherein the plug has a grip portion with a cross shape in plan which has four protruding portions, and the plug is rotatable between a first position and a second position, the first position being a position in which one of the flow paths connects the first port and the second port and the other flow path connects the third port and the fourth port, and the second position being a position in which one of the flow paths connects the first port and the fourth port and the other flow path connects the second port and the third port, the four protruding portions of the grip portion and the four ports extend in a same direction overlap each other as viewed in plan when the plug is located at the first position and the second position, the first port connects upstream of a vascular access, the third port connects downstream of the vascular access, the second port connects upstream of a machine, the fourth port connects downstream of the machine, at least one of the first port, a tube connected to the first port, and a cover fitted to the first port or the tube has a first indicator, one of the four protruding portions which overlaps the first port in the first position has a second indicator, and the first and second indicator are configured as an indication mechanism enabling an operator to visually observe a normal flow direction or a reverse flow direction, in the normal flow direction, blood is drawn from upstream of the vascular access to upstream of the machine via the first port and the second port and is returned to downstream of the vascular access via the fourth port and the third port, in the reverse flow direction, blood is drawn from downstream of the vascular access to upstream of the machine via the third port and the second port and is returned to upstream of the vascular access via the fourth port and the first port.

7. A flow path switching device, comprising:

a body including an outer cylinder and a plug, the outer cylinder having a first port, a second port, a third port, and a fourth port which are provided at regular intervals along its outer circumference, the plug being accommodated in the outer cylinder such that the plug can slide and rotate therein, and the plug having two flow paths independent of each other and each connecting adjacent two of four openings formed at regular intervals in a side surface of the plug, wherein the plug has an upper recess for visual recognition in its upper surface and a bottom recess for visual recognition in its, the flow paths are visually recognizable through the upper and bottom recesses for visual recognition and functions as an indicator indicating which one of the second port and the third port the first port connects to and which one of the second port and the third port the fourth port connects to.

* * * * *